(12) United States Patent
Sammes et al.

(10) Patent No.: US 7,416,802 B2
(45) Date of Patent: Aug. 26, 2008

(54) ELECTRODE-SUPPORTED SOLID STATE ELECTROCHEMICAL CELL

(75) Inventors: Nigel Sammes, Wrentham, MA (US);
Tracy Murray, Wrentham, MA (US);
Michael Brown, Norwood, MA (US);
Warren Ziegler, Norfolk, MA (US)

(73) Assignee: Acumentrics Corporation, Westwood, MA (US)

( * ) Notice: Subject to any disclaimer, the term of this patent is extended or adjusted under 35 U.S.C. 154(b) by 500 days.

(21) Appl. No.: 09/864,070

(22) Filed: May 22, 2001

(65) Prior Publication Data

US 2002/0028367 A1  Mar. 7, 2002

Related U.S. Application Data

(60) Provisional application No. 60/206,456, filed on May 22, 2000.

(51) Int. Cl.
*H01M 8/12* (2006.01)
*H01M 4/00* (2006.01)
*C25B 9/00* (2006.01)
*C25C 7/00* (2006.01)
*B05B 5/12* (2006.01)

(52) U.S. Cl. .............. 429/31; 429/44; 429/30; 429/33; 204/260; 204/424; 264/563; 427/115

(58) Field of Classification Search .......... 429/31, 429/44, 30, 33; 204/260, 424; 264/563; 427/115
See application file for complete search history.

(56) References Cited

U.S. PATENT DOCUMENTS 3,525,646 A  8/1970  Tannenberger et al. ........ 136/86

(Continued)

FOREIGN PATENT DOCUMENTS

EP  0442742 B1  5/1985

(Continued)

OTHER PUBLICATIONS

Kato et al., Anode-supported tubular sofcs operated at intermediate temperature, Oct. 7, 2000, Electrotechnical Laboratory pp. 553-560.*

(Continued)

*Primary Examiner*—Patrick Ryan
*Assistant Examiner*—Angela Martin
(74) *Attorney, Agent, or Firm*—Bromberg & Sunstein LLP

(57) ABSTRACT

A process for manufacturing a solid oxide fuel cell comprises, in one embodiment according to the invention: forming a plastic mass comprising a mixture of an electrolyte substance and an electrochemically active substance; extruding the plastic mass through a die to form an extruded tube; and sintering the extruded tube to form a tubular anode capable of supporting the solid oxide fuel cell. The process may further comprise, after sintering the extruded tube, layering an electrolyte onto the tubular anode; and, after layering the electrolyte, layering a cathode onto the electrolyte.

In a further related embodiment, the process further comprises co-extruding more than one anode layer to form the tubular anode. Each of the anode layers may comprise a ratio of electrochemically active substance to electrolyte substance, with such ratios being higher for layers that are layered further from a surface of the anode that contacts a fuel gas than for layers that are layered closer to the fuel gas.

Anode-supported tubular solid oxide fuel cells, which may be formed by such processes, are also disclosed. Additionally, electrode-supported oxygen pumps and oxygen sensors, and methods of manufacturing them, are disclosed.

14 Claims, 7 Drawing Sheets

U.S. PATENT DOCUMENTS

| | | | | |
|---|---|---|---|---|
| 4,374,184 | A | 2/1983 | Somers et al. | 429/17 |
| 4,490,444 | A | 12/1984 | Isenberg | 429/31 |
| 4,729,931 | A | 3/1988 | Grimble | 429/17 |
| 4,751,152 | A | 6/1988 | Zymboly | 429/31 |
| 4,791,035 | A | 12/1988 | Reichner | 429/31 |
| 4,808,491 | A | 2/1989 | Reichner | 429/13 |
| 4,888,254 | A | 12/1989 | Reichner | 429/31 |
| 5,035,962 | A | 7/1991 | Jensen | 429/40 |
| 5,082,751 | A | 1/1992 | Reichner | 429/19 |
| 5,085,742 | A | 2/1992 | Dollard et al. | 205/188 |
| 5,108,850 | A | 4/1992 | Carlson et al. | 429/31 |
| 5,143,801 | A | 9/1992 | Bates | 429/33 |
| 5,338,623 | A | 8/1994 | Nachlas et al. | 429/31 |
| 5,342,703 | A | 8/1994 | Kawasaki et al. | 429/30 |
| 5,368,667 | A | 11/1994 | Minh et al. | 156/89 |
| 5,368,951 | A | 11/1994 | Shiratori et al. | 429/30 |
| 5,395,704 | A | 3/1995 | Barnett et al. | 429/30 |
| 5,458,989 | A | 10/1995 | Dodge | 429/31 |
| 5,527,633 | A | 6/1996 | Kawasaki et al. | 429/30 |
| 5,589,017 | A | 12/1996 | Minh | 156/87 |
| 5,741,605 | A | 4/1998 | Gillett et al. | 429/31 |
| 5,788,788 | A | 8/1998 | Minh | 156/62.2 |
| 5,827,620 | A * | 10/1998 | Kendall | 429/31 |
| 5,908,713 | A * | 6/1999 | Ruka et al. | 429/31 |
| 5,916,700 | A * | 6/1999 | Ruka et al. | 429/30 |
| 5,993,985 | A | 11/1999 | Borglum | 429/30 |
| 5,998,056 | A | 12/1999 | Divisek et al. | 429/41 |
| 6,060,188 | A * | 5/2000 | Muthuswamy et al. | 429/31 |
| 6,221,522 | B1 | 4/2001 | Zafred et al. | 429/31 |
| 6,228,521 | B1 | 5/2001 | Kim et al. | 429/33 |
| 6,436,565 | B1 * | 8/2002 | Song et al. | 429/31 |
| 6,551,735 | B2 | 4/2003 | Badding et al. | 429/31 |
| 6,841,284 | B2 | 1/2005 | Brown et al. | 429/31 |
| 6,998,187 | B2 | 2/2006 | Finnerty et al. | 429/31 |
| 2003/0134170 | A1 | 7/2003 | Sarkar et al. | 429/31 |
| 2004/0247972 | A1 | 12/2004 | Kendall et al. | 429/31 |
| 2005/0042490 | A1 | 2/2005 | Finnerty et al. | 429/31 |

FOREIGN PATENT DOCUMENTS

| | | |
|---|---|---|
| EP | 0055016 | 7/1985 |
| EP | 0055011 B1 | 2/1987 |
| EP | 0 372 680 B1 | 6/1990 |
| EP | 0264688 | 7/1991 |
| EP | 0468698 A1 | 1/1992 |
| EP | 0562724 | 9/1993 |
| EP | 0505184 B1 | 6/1997 |
| JP | 04012461 | 1/1992 |
| JP | 04014766 | 1/1992 |
| JP | 05343079 | 12/1993 |
| WO | WO 99/17390 | 4/1999 |
| WO | WO 01/24300 A1 | 9/2000 |

OTHER PUBLICATIONS

Stover et al., Recent developments in anode supported thin film sofc at Research Centre Julich, Electrochemical Society Proceedings, vol. 99-19, pp. 812-821.*

Kim et al., Polarization effects in intermediate temperature, anode-supported solid oxide fuel cells, 1999, Journal of The Electrochemical Society, 146 (1), 69-78.*

Kim et al., The effect of anode thickness on the performance of anode-supported solid oxide fuel cells, Electrochemical Society Proceedings, 99 (19), 830-839.*

Primdahl et al., Thin anode supported sofc, Electrochemical Society Proceedings, 99 (19), 793-802.*

Kato et al, Anode-Supported Tubular SOFCs Operated at Intermediate Temperature, Electrochemical Laboratory.

Song et al., "Fabrication and Characteristics of Anode-Supported Tube For Solid Oxide Fuel Cell," *Electrochemical Society Proceedings*, vol. 99-19, 845-850.

Primdahl et al., "Thin Anode Supported SOFC," *Electrochemical Society Proceedings*, vol. 99-19, 793-802.

Kim et al., "Polarization Effect in Intermediate Temperature, Anode-Supported Solid Oxide Fuel Cells," *Journal of The Electrochemical Society*, 146(1) 69-78 (1999).

Kim et al., "The Effect of Anode Thickness on The Performance of Anode-Supported Solid Oxide Fuel Cells," *Electrochemical Society Proceedings*, vol. 99-19, 830-839 (1999).

Stöver et al., "Recent Developments in Anode Supported Thin Film SOFC at Research Centre Jülich," *Electrochemical Society Proceedings*, vol. 99-19, 812-821.

C. Hatchwell et al., *Current Collectors for a Novel Tubular Design of Solid Oxide Fuel Cell*, Journal of Power Sources, Elsevier, Amsterdam, NL, vol. 77, No. 1, pp. 64-68, Jan. 1999.

* cited by examiner

ELECTRODE-SUPPORTED SOLID STATE ELECTROCHEMICAL CELL

CROSS-REFERENCE TO RELATED APPLICATION

This application claims the benefit of our provisional application Ser. No. 60/206,456, filed May 22, 2000, the disclosure of which is hereby incorporated herein by reference.

TECHNICAL FIELD

This invention relates to solid state electrochemical cells; and in particular to fuel cells, oxygen sensors, and oxygen pumps, and methods of manufacture.

BACKGROUND OF THE INVENTION

Worldwide forecasts show electricity consumption increasing dramatically in the next decades, largely due to economic growth in developing countries that lack national power grids. This increased consumption, together with the deregulation of electrical utilities in industrialized nations, creates the need for small scale, distributed generation of electricity.

Fuel cells are a promising technology for providing distributed generation of electricity. A fuel cell places an oxidizing gas, such as air, and a hydrogen-containing fuel, such as hydrogen or natural gas, on opposite sides of an electrolyte in such a way that they combine to form water and electricity. Such a reaction requires a cathode and an anode composed of porous materials, and an ionically-conducting electrolyte. In solid oxide fuel cells, the electrolyte conducts negatively-charged oxygen ions.

Solid oxide fuel cell systems can be made less expensively than other kinds of fuel cells, and thus have particular potential for facilitating distributed power generation.

SUMMARY OF THE INVENTION

In one embodiment according to the invention, a process for manufacturing a solid oxide fuel cell comprises: forming a plastic mass comprising a mixture of an electrolyte substance and an electrochemically active substance; extruding the plastic mass through a die to form an extruded tube; and sintering the extruded tube to form a tubular anode capable of supporting the solid oxide fuel cell. The process may further comprise, after sintering the extruded tube, layering an electrolyte onto the tubular anode; and, after layering the electrolyte, layering a cathode onto the electrolyte.

In a further related embodiment, the process comprises reducing an oxide of an electrochemically active substance in the anode, to form pores. The reduction may comprise flowing a reducing gas over a surface of the anode, including flowing hydrogen gas over the surface of the anode at a temperature between 800° C. and 1000° C.

In another related embodiment, the process comprises milling a catalyst with the electrochemically active substance. The catalyst may comprise a material chosen from the group consisting of: $CeO_2$, ruthenium, rhodium, rhenium, palladium, scandia, titania, vanadia, chromium, manganese, iron, cobalt, nickel, zinc, and copper. The catalyst may also comprise $CeO_2$ in a proportion of between 1% and 3% by weight.

In another related embodiment, the process comprises forming a mass comprising a mixture of stabilized zirconia and nickel oxide. Layering the electrolyte may further comprise spraying or dip-coating a stabilized zirconia electrolyte onto the tubular anode. Layering the cathode may further comprise spraying a strontia-doped lanthanum manganite cathode onto the electrolyte.

In another related embodiment, layering the cathode, after layering the electrolyte, and after sintering the anode, comprises forming a tubular fuel cell in which a thickness of the anode comprises over 50% of a total thickness of the anode, the electrolyte, and the cathode. In another embodiment, sintering comprises forming a tubular anode with a thickness in the range of 300 µm to 400 µm.

In another related embodiment, the tubular anode comprises a uniform ratio of electrochemically active substance to electrolyte substance, and may contain a volume percentage of nickel of between 40% and 50%.

In a further related embodiment, the process further comprises co-extruding more than one anode layer to form the tubular anode. Each of the anode layers may comprise a ratio of electrochemically active substance to electrolyte substance, with such ratios being higher for layers that are layered further from a surface of the anode that contacts a fuel gas than for layers that are layered closer to the fuel gas. The electrochemically active substance may be nickel and the electrolyte substance may be stabilized zirconia. There may be two or more anode layers. The more than one anode layers may comprise a thicker support layer and a thinner active layer, the support layer being in contact with a fuel gas. The support layer may comprise a higher ratio of stabilized zirconia to nickel, while the active layer comprises a lower such ratio; for example, the support layer may comprise from 0% to 50% nickel by volume, while the active layer comprises from 40% to 45% nickel by volume. The process may comprise extruding the active layer around a current-collecting wire. The support layer may also comprise aluminum oxide.

In another embodiment, the extruded tube has a non-circular cross-section.

In a further embodiment, a process for manufacturing a solid oxide fuel cell comprises: forming first and second plastic masses, each plastic mass comprising a mixture of an electrolyte substance and an electrochemically active substance, the first plastic mass having a higher relative content ratio of electrochemically active substance to electrolyte substance, and the second plastic mass having a lower relative content ratio of electrochemically active substance to electrolyte substance; extruding the first plastic mass through a die to form a first extruded tube; extruding the second plastic mass through a die to form a second extruded tube; fitting the first extruded tube inside the second extruded tube to form a combined tube; and sintering the combined tube to form a tubular anode capable of supporting the solid oxide fuel cell. Each plastic mass may comprise a mixture of stabilized zirconia and nickel oxide, with the first plastic mass having a higher relative content ratio of nickel oxide to stabilized zirconia, and the second plastic mass having a lower relative content ratio of nickel oxide to stabilized zirconia.

In another embodiment, a tubular solid oxide fuel cell comprises: a cathode; an electrolyte; and a tubular anode capable of supporting the fuel cell. The anode may comprise a mixture of stabilized zirconia and nickel, and the electrolyte may comprise stabilized zirconia. The cathode may comprise a strontia-doped lanthanum manganite. A thickness of the anode may comprise over 50% of a total thickness of the anode, the electrolyte, and the cathode. The anode may have a thickness in the range of 300 µm to 400 µm. The anode may comprise a catalyst material chosen from the group consisting of: $CeO_2$ (which may be in a proportion of between 1% and 3% by weight), ruthenium, rhodium, rhenium, palladium, scandia, titania, vanadia, chromium, manganese, iron, cobalt, nickel, zinc, and copper. The anode may comprise a volume percentage of nickel of between 40% and 50%.

In a further, related embodiment, the anode comprises more than one anode layer, each layer having a different composition. In one such embodiment, the ratio of electrochemically active substance to electrolyte substance in each of the anode layers is higher for layers that are layered further from a surface of the anode that contacts a fuel gas than for layers that are layered closer to the fuel gas. The electrochemically active substance may be nickel and the electrolyte substance may be stabilized zirconia. There may be two or more anode layers.

In a further, related embodiment, the more than one anode layers comprise a thicker support layer and a thinner active layer, the support layer being in contact with a fuel gas. The support layer may comprise a higher ratio of stabilized zirconia to nickel, and the active layer may comprise a lower such ratio. The support layer may comprise from 0% to 50% nickel by volume, and the active layer may comprise from 40% to 45% nickel by volume. The active layer may comprise an embedded current-collecting wire. The support layer may comprise aluminum oxide.

In another embodiment, the tubular anode has a non-circular cross-section.

In another embodiment, an electrode-supported oxygen pump or oxygen sensor comprises: a first tubular electrode layer capable of supporting the oxygen pump or sensor; an electrolyte layer, layered on the first electrode layer; and a second tubular electrode layer layered on the electrolyte layer. The first tubular electrode layer may comprise an electrolyte substance mixed with a precious metal, which may be chosen from the group consisting of: platinum, palladium, silver, rhodium, and rhenium. The electrolyte substance may comprise stabilized zirconia. The first tubular electrode layer may also comprise a porous perovskite substance, such as doped $LaCoO_3$ or doped $La[CoFe]O_3$.

In a further related embodiment, the electrolyte layer comprises stabilized zirconia. The electrolyte layer may also comprise a thinner layer of stabilized zirconia and a thicker porous support layer, which may comprise alumina. The electrolyte layer may also comprise a doped oxide, the oxide being chosen from the group consisting of: cerium oxide, lanthanum oxide, bismuth oxide, yttrium oxide, and lead oxide. The electrolyte layer may also comprise a porous perovskite, such as doped $LaCoO_3$ or doped $La[CoFe]O_3$.

In another embodiment, a method of manufacturing an oxygen pump or oxygen sensor comprises: extruding a first tubular electrode, capable of supporting the oxygen pump or sensor; layering an electrolyte layer on the first tubular electrode; and layering a second tubular electrode on the electrolyte layer. The first tubular electrode may comprise a precious metal chosen from the group consisting of: platinum, palladium, silver, rhodium, and rhenium. Also, the first tubular electrode may comprise a porous perovskite.

In another embodiment, a method of manufacturing an oxygen pump or oxygen sensor comprises: extruding a tubular electrolyte layer comprising cerium oxide; and reducing an outside and an inside surface of the electrolyte layer.

DESCRIPTION OF SPECIFIC EMBODIMENTS

Embodiments of the present invention allow the production of solid state electrochemical cells that have a lower electrical resistance than such systems have had in the past; that are less expensive; and that achieve faster response times.

Figure 1A:
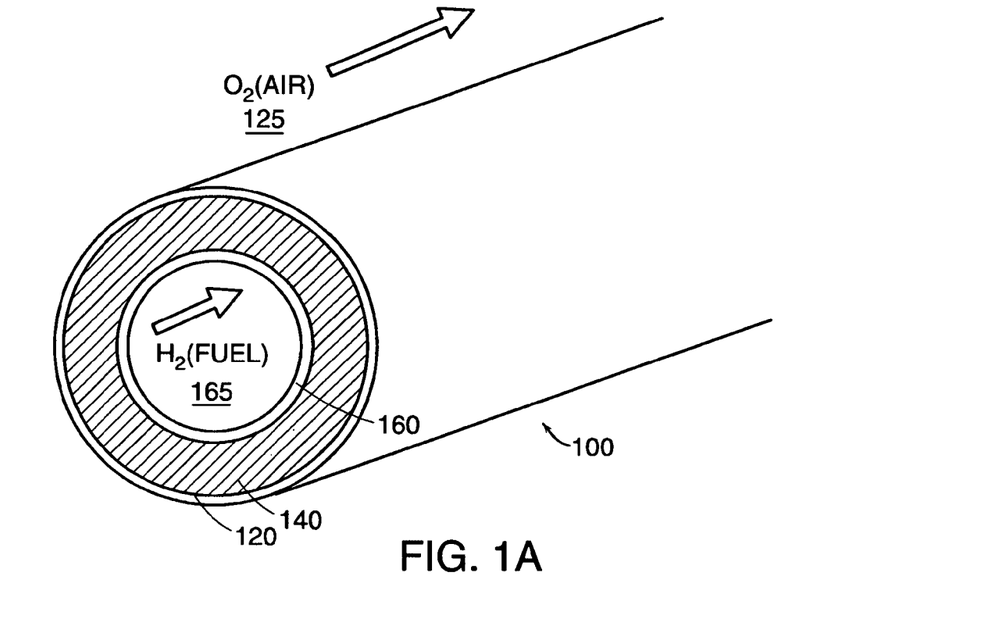
FIGS. 1A and 1B show cross-sectional isometric and cross-sectional views, respectively, of an electrolyte-supported tubular solid oxide fuel cell.
Figure 1B:
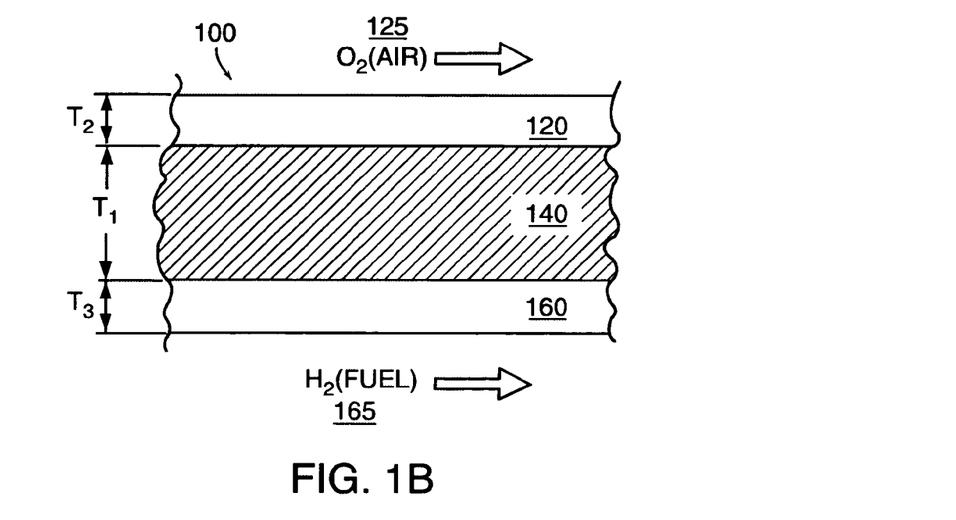

FIGS. 1A and 1B show cross-sectional isometric and cross-sectional views, respectively, of an electrolyte-supported tubular solid oxide fuel cell 100. Tubular cell 100 is formed by three concentric tubular layers 120, 140, and 160. The middle, electrolyte layer 140 performs two functions: first, it provides mechanical support for cell 100; and second, it provides an ionic conduction pathway for negatively-charged oxygen ions. These oxygen ions are produced by an oxidizing gas 125 (such as oxygen, present in air) that surrounds the tube's outer diameter. The electrolyte conducts the oxygen ions from the outer, cathode layer 120 to the inner, anode layer 160, each of which layers is formed from a porous substance. A source of hydrogen 165, such as hydrogen gas ($H_2$) or natural gas, is passed through the hollow center of the cell 100 and reacts with the oxygen ions to produce water and electricity. The cathode 120 and anode 160 are connected to terminals (not shown) for conducting electrical current to and from the cell.

In cell 100, electrolyte 140 is formed from a ceramic such as yttria-doped stabilized zirconia (YSZ). Electrolyte 140 has a thickness $T_1$ of about 200 μm that enables it to provide mechanical support for cell 100; the cell is therefore an electrolyte-supported cell. Once the electrolyte has been formed, cathode 120 is typically sprayed onto the outside of electrolyte 140 to a thickness $T_2$ of about 50 μm to 100 μm; and anode 160 is sprayed onto the inside of electrolyte 140 to a thickness $T_3$ of about 50 μm.

A disadvantage of cell 100 is that electrolyte 140 must be thick enough to support the cell mechanically. According to Ohm's law, the resistance across an electrolyte of thickness 1, resistivity ρ, and cross-sectional area A is given by:

$$R = \frac{\rho l}{A} \quad \text{\{Equation 1\}}$$

It follows from Equation 1 that an electrolyte of greater thickness (l) has a higher electrical resistance (R). Since, in cell 100, electrolyte 140 must be thick enough to support the cell, it has a high value of l and thus a greater resistance. Since power losses are proportional to resistance, more cells 100 must be used, to produce a given power output, than would have to be used if cell 100 had a lower resistance. Thus fuel cell systems using such cells are more expensive than they would be otherwise. Also, since the fuel cell reaction occurs at high temperature, the start-up time of a fuel cell system is limited by the time that it takes for the cells to heat up to the reaction temperature. Systems containing more cells for a given power output require longer to heat up, and thus longer to start. Systems containing electrolyte-supported cells 100 are thus larger, more expensive, and slower to start than they would be if cell 100 had a lower resistance.

Attempts have been made to solve this problem by using materials for electrolyte 140 that have a lower resistivity $\rho$ (see Equation 1). Materials containing $CeO_2$, $Bi_2O_3$, and $LaGaO_3$ (along with secondary dopants) have produced dramatic reductions in resistivity $\rho$. However, these materials have disadvantages in other characteristics. $CeO_2$ reduces easily to $CeO_{2(-x)}$; $Bi_2O_3$ melts at low temperatures and is extremely volatile; $LaGaO_3$ suffers from evaporation of Ga; and all three are mechanically weak. Most notably, however, all three are presently expensive: $LaGaO_3$ costs about 1000 times as much as yttria-stabilized zirconia (YSZ).

Another fuel cell design is found in U.S. Pat. No. 5,998,056 of Divisek et al., which discloses an anode substrate for a planar fuel cell. Planar fuel cells suffer from several disadvantages by comparison with tubular fuel cells. In particular, because of their planar shape, they are difficult to seal to prevent gas leaks.

Other designs use cathode-supported tubular fuel cells. These, however, are relatively expensive.

Figure 2A:
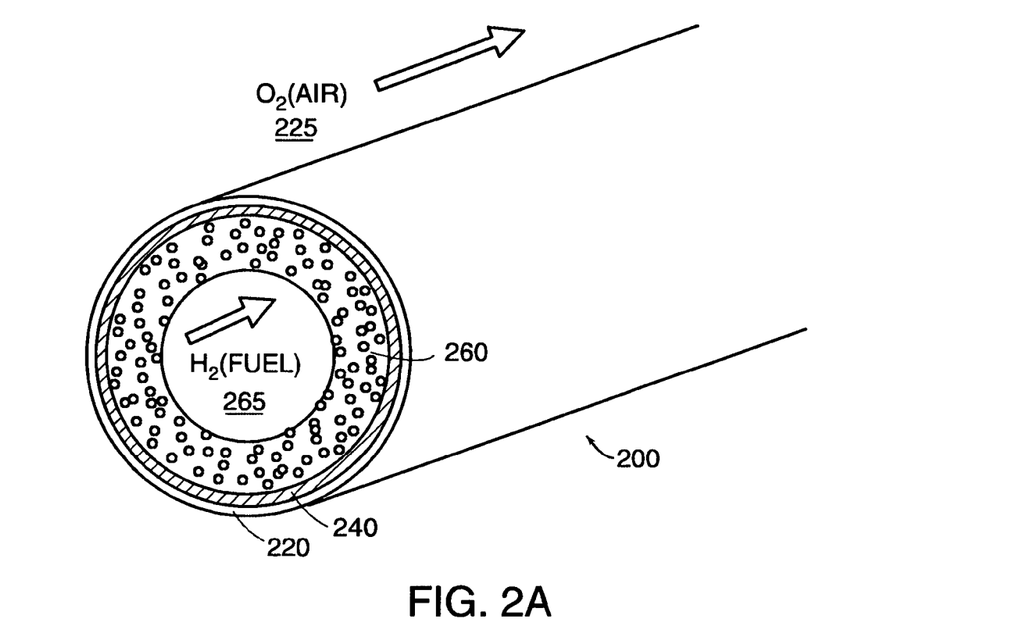
FIGS. 2A and 2B show cross-sectional isometric and cross-sectional views, respectively, of an anode-supported fuel cell according to an embodiment of the invention.
Figure 2B:
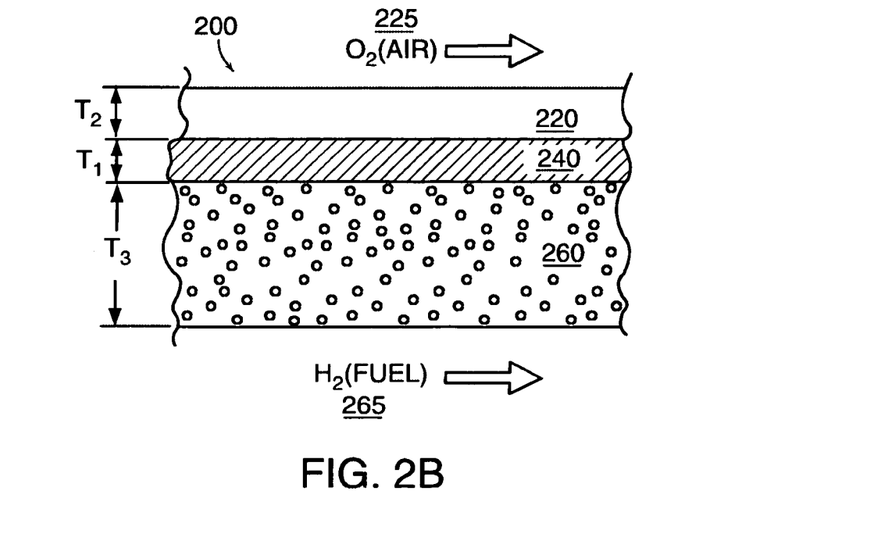

The disadvantages of these designs are overcome by the anode-supported tubular fuel cell shown in FIGS. 2A (cross-sectional isometric view) and 2B (cross-sectional view), according to an embodiment of the invention. In this embodiment, tubular solid oxide fuel cell 200 is mechanically supported by a thick anode layer 260, upon which thin electrolyte layer 240 and cathode layer 220 are formed. Since fuel cell 200 is mechanically supported by anode 260, there is no need for a thickened electrolyte layer to support the cell, and the electrolyte layer 240 may be reduced in thickness (l) as compared with the thickness of the electrolyte of an electrolyte-supported fuel cell. As follows from Equation 1, a lower thickness (l) means that fuel cell 200 has a lower resistance. For the reasons described above, a fuel cell system that can incorporate such cells, which have a lower resistance, is less expensive, more compact, and faster to start than electrolyte-supported systems. It also avoids the expense of cathode-supported fuel cells. Additionally, it can avoid disadvantages with sealing found in planar systems, because tubular fuel cells according to embodiments of the invention may be mounted in holes in a base plate, and used with their ends open (though open ends are not required—embodiments may also have a closed end on the fuel cell). Thus, anode-supported fuel cells in accordance with embodiments of the invention provide advantages over conventional designs, in both cost and performance, that are improvements for the distributed generation of electricity.

Fuel cell 200, according to an embodiment of the invention, reacts negative oxygen ions from an oxidizing gas 225 (such as the oxygen found in air) with hydrogen found in fuel 265 (which may be hydrogen gas, natural gas, a hydrocarbon gas, or another source of hydrogen). Oxygen ions pass through porous cathode layer 220 and are ionically conducted through electrolyte layer 240 to the porous cell-supporting anode layer 260, where they react with the fuel 265 to form electricity and water. Terminals (not shown) conduct electrical current to and from the cell.

As can be seen in FIG. 2B, thickness $T_1$ of electrolyte layer 240 is greatly reduced by comparison with thickness $T_3$ of anode layer 260, since electrolyte layer 240 does not need to provide mechanical support to the cell. The thickness of the anode layer, according to embodiments of the invention, may comprise 50% or more of the total thickness of the fuel cell wall ($T_1$ plus $T_2$ plus $T_3$), and the electrolyte layer may be correspondingly reduced in thickness.

Figure 3:
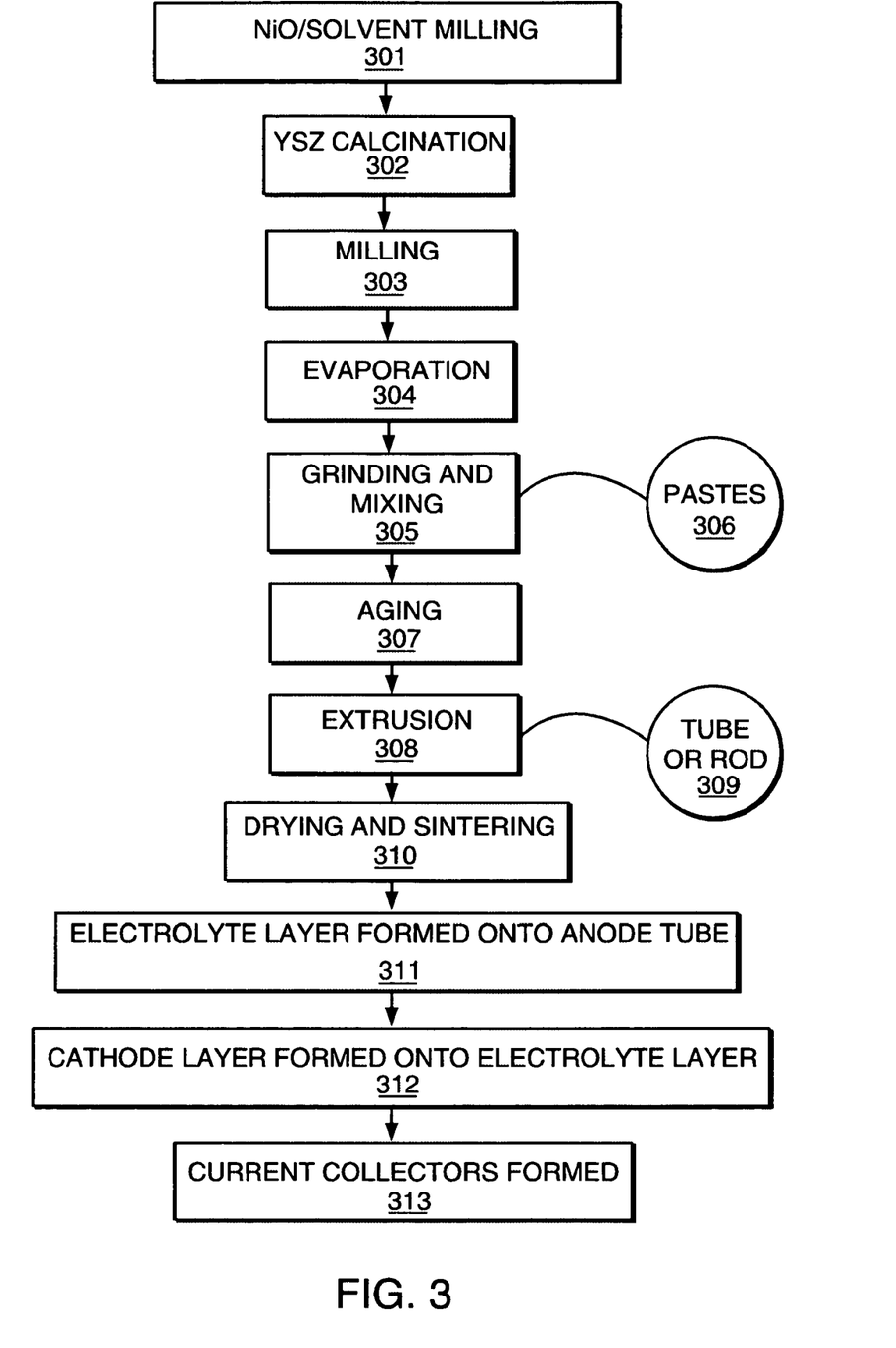
FIG. 3 shows a block diagram of a process for manufacturing a tubular solid oxide fuel cell in accordance with an embodiment of the invention.

FIG. 3 is a block diagram that summarizes a process for manufacturing a tubular solid oxide fuel cell in accordance with an embodiment of the invention. The solid ingredients of the cell's anode preferably include nickel oxide (NiO), which provides the electrochemical activity for the anode, and yttria-doped stabilized zirconia (YSZ) as an electrolyte substance. Other metals, instead of nickel, may provide electrochemical activity; for example, platinum, palladium, and cobalt may be used in accordance with embodiments of the invention. Also, other electrolyte substances may be used. In a preferred embodiment, the anode is made of a 50 vol % mixture of NiO and 8 mol % YSZ. In addition to an electrochemically active substance and an electrolyte substance, the anode is preferably fabricated using a binder system, a lubricant, a pH control agent, and solvents. In a preferred embodiment the binder system is the Duramax™ binder system, B-1051 and B1052, manufactured at the time of filing by Rohm and Haas Co. of Philadelphia, Pa.; the lubricant is PEG-400, manufactured at the time of filing by Union Carbide of Danbury, Conn.; the pH control agent is AMP-95, manufactured at the time of filing by Angis Chemicals of Buffalo Grove, Ill.; and the solvents are acetone, distilled water, or isopropyl alcohol.

In describing the process of the embodiment of FIG. 3, a specific embodiment of a process is described; those of ordinary skill in the art will recognize, however, that variations from this process are possible in accordance with embodiments of the invention.

In step 301 of the process of the embodiment of FIG. 3, NiO powder is milled in a solvent (preferably isopropyl alcohol) by roller mill in 250 ml Nalgene containers with 10 mm diameter zirconia grinding media, for 48 hours. In step 302, YSZ powder is heat treated at 900° C. for 2 hours to reduce the powder surface area. In step 303, the YSZ powder is added to the NiO powder and milled a further 24 hours. The milled powders are next dried by evaporating off the solvent in an oven at 75° C. for 12 hours, in step 304. A particle size analysis is performed on the resulting powders using a laser diffraction particle sizer (such as one sold at the time of filing as the Malvern Mastersizer) to determine the effect of the solvent on particle size, and the distribution of particle sizes. In step 305, the powders are hand ground and mixed with the additives—binders, lubricants, pH control agents, and solvents (here, preferably water)—to produce pastes 306; other additives may include plasticizers, deflocculants, catalysts, and other ingredients. The pastes are next aged overnight in plastic bags to produce extrudable pastes (step 307).

Next, in step 308 of the embodiment of FIG. 3, the extrudable pastes are extruded through a die into a tube or rod form 309, using a high strength steel piston extruder coupled to a tensile testing machine (such as a Lloyd LR100K tensile testing machine). The piston speed is controlled by a personal computer, and preferably set at a rate of 3 mm per minute. Following extrusion, the extruded tubes are dried horizontally on a V-shaped alumina sample holder for 24 hours and then sintered in air in a chamber furnace (such as a furnace manufactured at the time of filing by Ceramic Engineering) (step 310). A furnace temperature ramp rate of 0.5° C. per minute, up to 500° C., is used to burn off the organic substances; this is followed by a ramp rate of 3° C. per minute up to 1300° C., and a dwell time of 2 hours for sintering. The result is a set of anode tubes (one made from each extruded tube) each capable of supporting a fuel cell; in one embodiment, an anode has a thickness in the range of 300 μm to 400 μm.

Next, in step 311, an electrolyte layer is coated onto the anode tube. The electrolyte layer may be formed of yttria-doped stabilized zirconia (YSZ), and may be sprayed, dip-coated, or otherwise layered onto the anode tube. Preferably, a YSZ slurry is prepared using the electrode ink methodology, and a thin coating is then sprayed onto the sintered anode support tube to form an electrolyte layer. The electrolyte layer is then dried in air and isostatically pressed at 200 MPa. Finally the electrolyte layer is sintered at 1350° C. for 2 hours to form a fully dense membrane of about 20 μm thickness.

Next, in step 312, a cathode layer is coated onto the electrolyte layer. The cathode layer is preferably made from strontia-doped lanthanum manganite ($LaMnO_3$), but may also be made from gadolinium manganate, a cobaltate, or other substances. In a preferred embodiment, two cathode layers are applied to the outside of the electrolyte layer by using a spray gun to form thin, even cathode layers on the electrolyte layer's surface. The first (inner) cathode layer is preferably a mixture, 50/50 wt % of $La_{0.80}Sr_{0.20}MnO_3$ (Rhodia, 99.9% pure) with 8 mol % YSZ (Tosoh). The second cathode layer is preferably only $La_{0.80}Sr_{0.20}MnO_3$ (Rhodia, 99.9% pure).

Finally, in step 313, current collectors are connected to the anode and cathode layers to complete the fuel cell's fabrication. The cathode current collector is preferably made of silver wire (Alfa 99.997% pure) of 0.25 mm diameter, and wound criss-cross along the anode length with close contact between windings. Silver paste (Alfa) is preferably painted onto the cathode and air dried, before the current collection is wound onto it. The anode current collector is preferably made of nickel wire (Alfa 99.98% pure) of 0.5 mm diameter, and is spiraled around a 1 mm diameter needle former to produce a tight coil. The coil is fed into the fuel cell by jamming inside the tube, to produce a good contact.

An example of preparation of cell-supporting anode tubes according to an embodiment of the invention is now provided. It should be recognized that this example is provided for the purpose of illustration, and should not be taken to limit the invention to the example given.

EXAMPLE 65.08 g of NiO powder was milled in 100 g isopropanol in a 1 L plastic milling container with 1 kg of 5 mm diameter milling media, at 25 Hz, for 42-48 hours, until a particle size of 0.8 μm was reached. 7.19 g of 8 mol % yttria stabilized zirconia (8YSZ) (which had been calcined for 2 hours at 900° C.), and 27.72 g 8YSZ (which had been calcined for 2 hours at 1100° C.), were added to the milling container and milled a further 6-8 hours, until an average particle size of 0.6 μm was reached.

The prepared slurry was then poured into a shallow tray and left to evaporate at room temperature for 12 hours. The resulting dried cake of material was further dried in an oven at 100° C. for 2 hours. The powder was milled to break up agglomerates.

50 g of the milled powder was then made into a dough. Additives were prepared by weight of ceramic powder. 2% polyethylene glycol-400 (PEG-400) was mixed with 4.5% distilled water, and then added to the powder and mixed for 2-3 minutes. Following that, 10% Duramax B-1051 and 2.5% B-1052 were blended together, and then mixed into the powder, mixing for 3-5 minutes. A further 7-10% distilled water and 1.5% AMP-95 was mixed into the powder, and mixed for approximately 10 minutes to form a dough. The dough was kneaded by hand for 1-2 hours before being left to age in a sealed plastic bag for 4-6 hours. The dough was kneaded again for approximately 30 minutes, and then passed through the extrusion die several times to ensure homogeneity. The dough was kneaded 5 minutes more before being extruded into tubes and enclosed in tube holders to dry for 24 hours. The tubes were then sintered for 2 hours at 1300° C.

In accordance with a further embodiment of the invention, no pore-forming substance is added to create the pores in the anode tube. Addition of a pore-forming substance creates the risk of changing the size of the tube when the pores form, and of creating cracks in the electrolyte layer. Thus, an embodiment according to the invention avoids the need to add a pore-forming substance. This embodiment involves first creating a fully dense, sintered system (which may be made, for example, in accordance with the process of the embodiment of FIG. 3, or the manufacturing process "Example"); and then reducing the nickel oxide (or other oxide of an electrochemically active substance) that is present in the anode, to form nickel (or other reduced form of an electrochemically active substance). The reduction may be performed, for example, by passing a reducing gas (such as hydrogen) through the cell, at the operating temperature of approximately 800 to 1000° C., after sintering the cell in air.

In accordance with another embodiment of the invention, catalysts may be added to the anode layer to facilitate reformation of a hydrocarbon fuel gas. Instead of spraying such catalysts onto the anode's surface, they may be added to the anode at the milling stage, and extruded with the anode, to allow in situ catalysis.

An example of a reaction occurring in a solid oxide fuel cell that uses a hydrocarbon fuel gas may be expressed, in a simplified form that ignores partial reactions, as:

$$O_{2-} + CH_4 \xrightarrow{\{Catalyst\ 1\}} CO + H_2 \xrightarrow{\{Catalyst\ 2\}} CO_2 + H_2O \quad \{Equation\ 2\}$$

Here, methane (CH4) is used as the hydrocarbon gas, but other hydrocarbons may be used. The first half reaction of Equation 2, a partial oxidation, may be catalyzed by $CeO_2$ (cerium), ruthenium, rhodium, rhenium, or palladium, or other catalysts in accordance with embodiments of the invention. By encouraging the reaction of Equation 2, such catalysts reduce harmful "coking" reactions, such as:

$$CH_4 \rightarrow C + 2H_2 \quad \{Equation\ 3\}$$

Such "coking" reactions can degrade performance by producing carbon deposits, and may result in a cell's anode lifting away from its electrolyte layer.

The second half reaction of Equation 2 may be catalyzed, in accordance with embodiments of the invention, by oxidation catalysts such as: scandia, titania, vanadia, chromium, manganese, iron, cobalt, nickel, zinc, and copper. A catalyst may be selected from amongst such catalysts in order to optimize performance with a particular hydrocarbon fuel. The simple oxide of these catalysts may be used, or a pyrochlore or perovskite form.

In accordance with embodiments of the invention, the catalysts described above are milled with the NiO/YSZ mixture, in a fashion similar to that described in steps 301 to 303 above. They can then be extruded along with the other ingredients of the anode layer, and used to produce in situ catalysis. Anywhere from 0 to 10% by weight of the catalysts in the anode is preferable, depending on the hydrocarbon fuel with which the catalyst is being used. About 2% by weight of $CeO_2$ is preferable for use with methane fuel. Instead of extruding the catalysts with the anode, they may alternatively be sprayed, co-extruded, or dip-coated onto the anode, in a thin layer.

Figure 4:
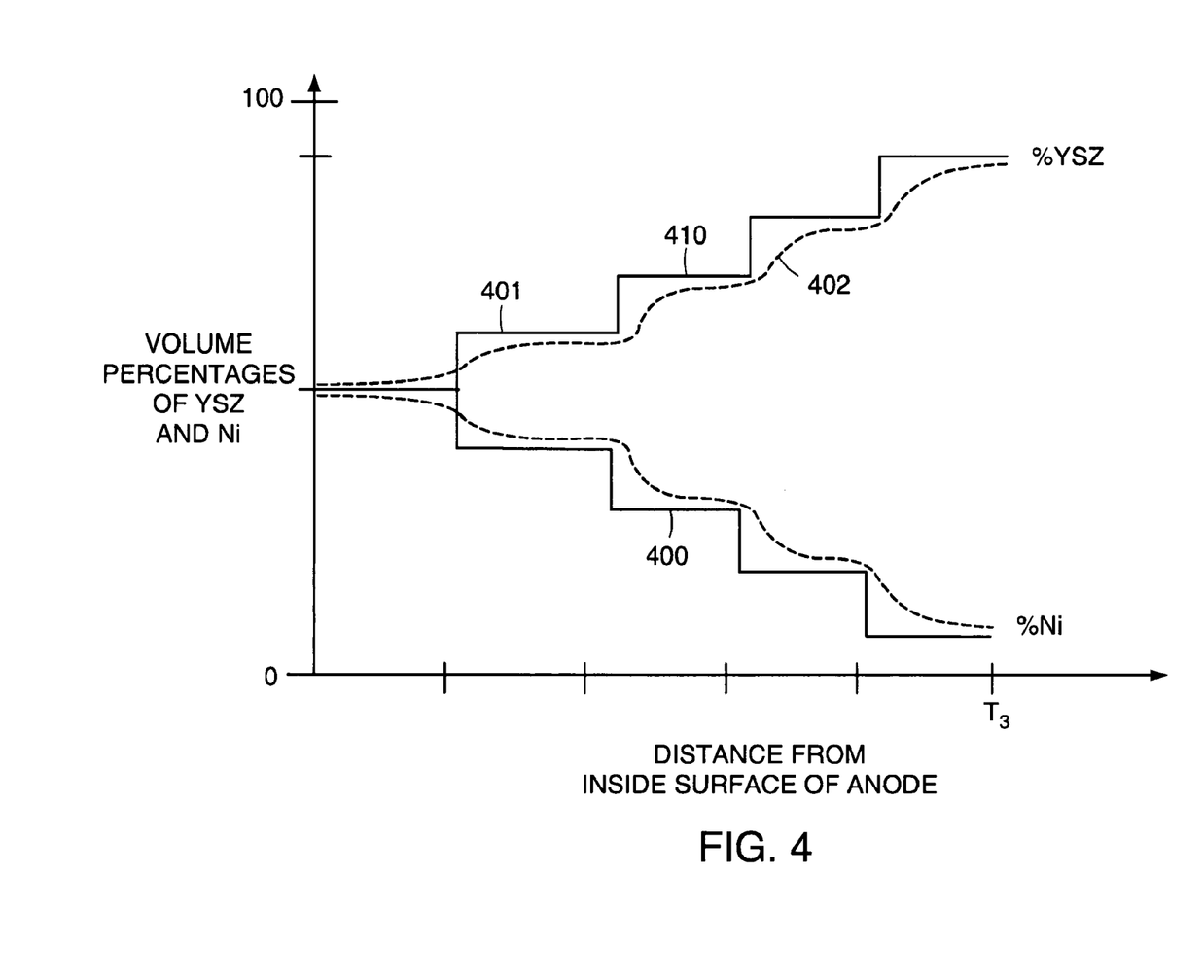
FIG. 4 shows a graph of chemical gradients in a co-extruded anode support of a fuel cell, according to an embodiment of the invention.

FIG. 4 shows a graph of chemical gradients in a co-extruded anode support of a fuel cell, according to an embodiment of the invention. In this embodiment, a process for manufacturing a solid oxide fuel cell involves similar steps to those described for FIG. 3 and the manufacturing process "Example," but the anode is formed by co-extrusion of more than one layer, each layer having different proportions of an electrochemically active substance and an electrolyte substance. An anode functions in a fuel cell by providing an electrochemically active substance. Typically, in a solid oxide fuel cell, the anode's active substance is nickel. If a pure nickel anode were formed on a fuel cell's electrolyte layer, however, the nickel layer would split away from the electrolyte layer upon heating, because the layers would have different thermal characteristics. Thus, in order to match the thermal characteristics of the electrolyte layer, it is desirable for higher proportions of electrolyte material to be present in the anode portions that are nearer the electrolyte layer. However, it is also desirable for higher proportions of the electrochemically active substance to be as close as possible to the hydrogen-containing fuel, to optimize performance.

An anode which satisfies both of these constraints thus has opposing gradients of the electrochemically active substance and the electrolyte substance, from the inner surface of the anode layer to the outer surface of the anode layer. FIG. 4 shows the volume percentages of nickel 400 (as an example of an electrochemically active substance) and yttria-stabilized zirconia (YSZ) 410 (as an example of an electrolyte substance), in an anode produced by a co-extrusion of multiple anode layers, in accordance with an embodiment of the invention. In the layer at the inner surface of the anode the volume percent of nickel 400 is highest, in order to produce high electrochemical activity, while the volume percent of YSZ 410 is lowest. But in the layers of the anode at further distances from the inner surface, the volume percent of YSZ 410 increases, in order to match the thermal characteristics of the electrolyte layer, while the volume percent of nickel 400 decreases. Solid lines 401 represent the proportions present before sintering; as can be seen, the layers form a step-like pattern of opposing gradients of YSZ and Ni. Migration of the substances during sintering may cause the actual proportions of the substances to be smoothed-out somewhat, as represented by dashed lines 402. Use of an increasing number of layers in the co-extruded anode thus allows approximation of a smoothly varying gradient of YSZ/Ni.

In accordance with embodiments of the invention, the proportions of electrochemically active substance and electrolyte substance in the cell-supporting anode need not vary as shown in FIG. 4, but may have other relative distributions of the two substances. For example, different numbers of layers may be co-extruded. In one embodiment, two anode layers are co-extruded, one of which has a relatively high ratio of electrochemically active substance to electrolyte substance and is of smaller diameter, and another of which has a relatively low ratio of electrochemically active substance to electrolyte substance and is of larger diameter.

Alternatively, the anode may have a composition with a uniform ratio of electrochemically active substance to electrolyte substance. In this embodiment, a total volume percentage of about 40-50% nickel in the anode layer is preferable. The anode layer may act to some degree as a current collector, as well as a support tube, in such a case, thereby eliminating the need to wrap a current-collecting wire throughout the inside of the fuel cell.

In another embodiment, the anode is formed by co-extruding a thicker support layer with a thinner active layer. In this case, the support layer has a high proportion of YSZ, and a low proportion of NiO (for example, from 0 to 50 Vol %); and is positioned at the inner surface of the anode. The thinner active layer has a higher proportion of NiO (for example, from 40-45%), and is positioned between the support layer and the electrolyte. In such a case, current collection may occur through the active layer; for example, the active layer may be extruded around a current-collecting wire. The thicker support layer may be formed of an electrolyte substance (such as YSZ), or may instead be formed of aluminum oxide.

Note that the particular substances (nickel and YSZ) and proportions shown in FIG. 4 should not be taken to limit the invention to the specified embodiment; other substances and proportions may be used in accordance with embodiments of the invention.

Figure 5:
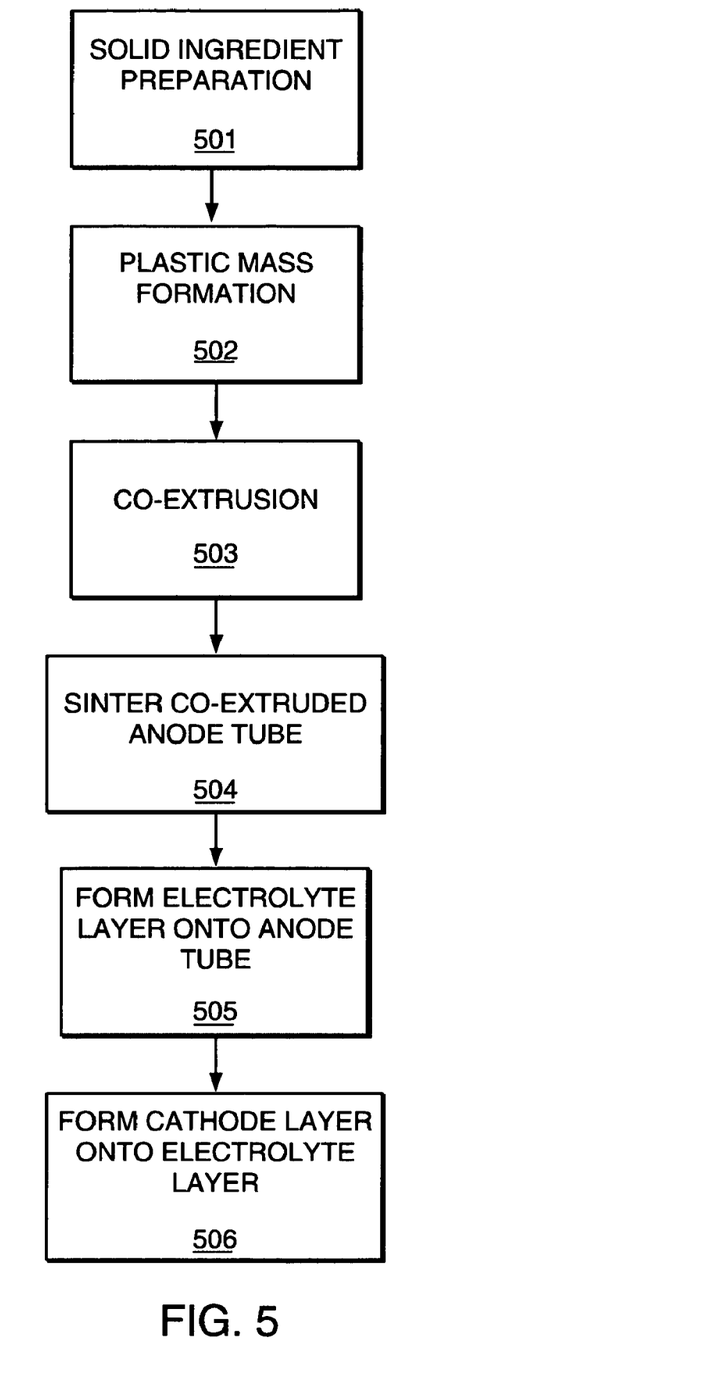
FIG. 5 shows a block diagram of a process for manufacturing a solid oxide fuel cell that includes co-extruding a cell-supporting anode, in accordance with an embodiment of the invention.

FIG. 5 shows a block diagram of a process for manufacturing a solid oxide fuel cell that includes co-extruding a cell-supporting anode, in accordance with an embodiment of the invention. In a similar fashion to that described for FIG. 3 and the manufacturing process "Example," the process involves first milling and grinding solid ingredients, in step 501. As above, these ingredients preferably include nickel oxide (NiO), which provides the electrochemical activity for the anode, and yttria-doped stabilized zirconia (YSZ). In accordance with one embodiment of the invention, here called a first example of a co-extrusion process, two mixtures of the ingredients are separately formed: one with a relatively high ratio of electrochemically active nickel to electrolyte YSZ, and one with a relatively low ratio of nickel to YSZ. As above, the substances are milled, ground, and analyzed for particle-size distribution. Alternatively, in a second example of a co-extrusion process, more than two mixtures having different compositions of nickel and YSZ are formed, which will subsequently be formed into multiple layers in the anode.

In step 502 of the process of the embodiment of FIG. 5 the anode's solid ingredients are formed into a plastic mass for co-extrusion. As above, this is performed by adding a solvent to the mixed solid ingredients, and adding other additives, and aging the mixture. In accordance with the first example of a co-extrusion process, two separate plastic masses are formed, one from the high-ratio solid mixture and one from the low-ratio solid mixture. Alternatively, in the second example of a co-extrusion process, more than two plastic masses are formed, that will subsequently be formed into multiple layers in the anode.

In step 503 of the embodiment of FIG. 5, plastic masses are co-extruded through a die to form an extruded anode tube. In the first example of a co-extrusion process, the high-ratio plastic mass may be extruded through a die of smaller diameter, at the same time that the low-ratio plastic mass is extruded through a die of larger diameter, that surrounds the first die. This produces a co-extruded anode tube with two concentric layers, one high in electrochemically active substance, the other high in electrolyte substance. Alternatively, the high-ratio and low-ratio plastic masses are separately extruded, with the high-ratio mass having a smaller diameter than the low-ratio mass; and then the resulting high-ratio extruded tube is fitted inside the resulting low-ratio extruded tube. This also produces an anode tube with concentric bi-layers. In the second example of a co-extrusion process, more than two plastic masses are co-extruded, through more than two dies that surround one other.

In step 504, the co-extruded anode tube is dried and sintered. The resulting anode, in one embodiment, has a thickness in the range of 300 µm to 400 µm. In steps 505 and 506, an electrolyte layer is coated onto the anode tube, and a cathode layer is coated onto the electrolyte layer, in a similar fashion to that described above.

Figures 6A, 6B:
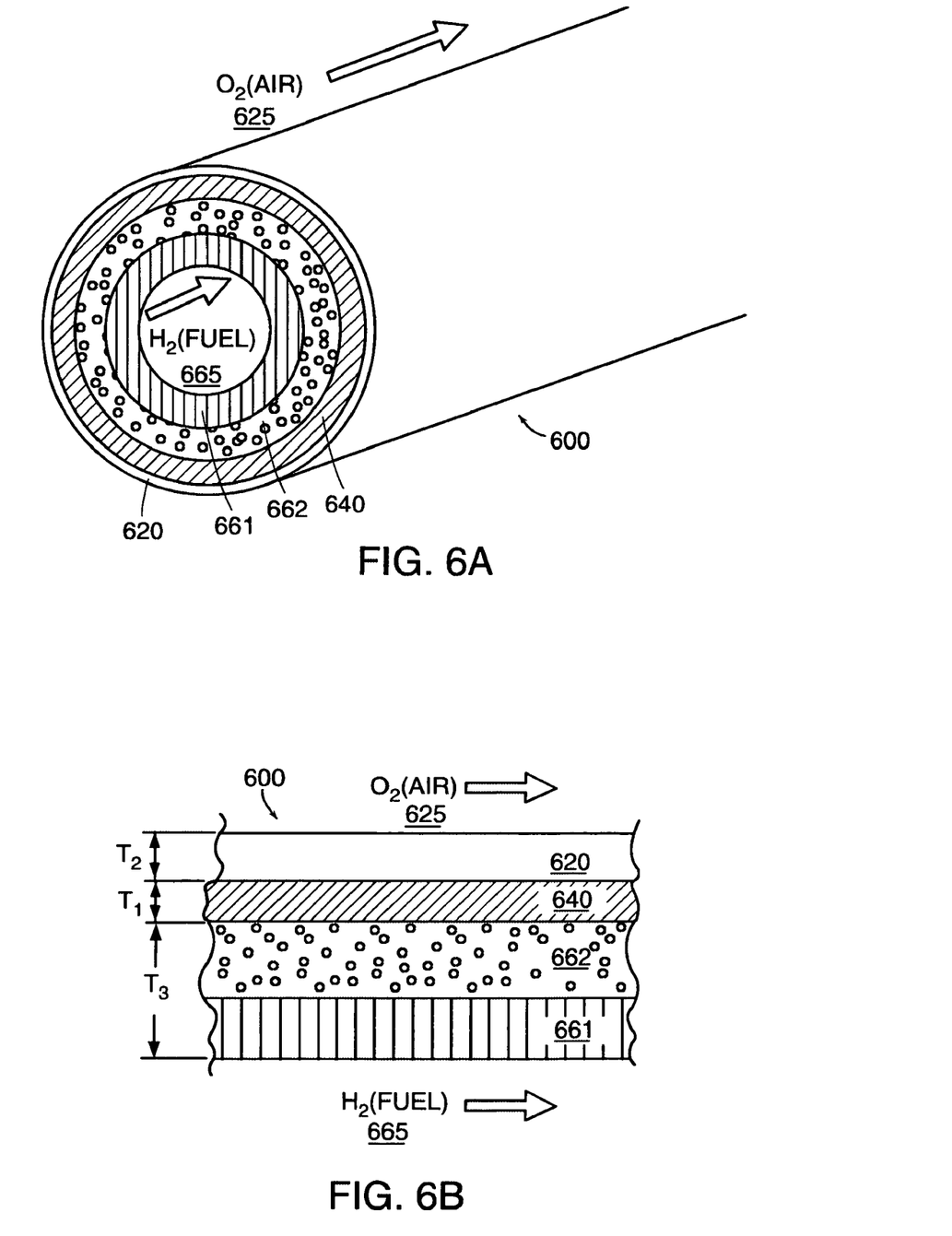
FIGS. 6A and 6B show an anode-supported tubular solid oxide fuel cell, in accordance with an embodiment of the invention, that may be manufactured by the co-extrusion process of FIG. 5.

FIGS. 6A and 6B show an anode-supported tubular solid oxide fuel cell 600, in accordance with an embodiment of the invention, that may be manufactured by the co-extrusion process of FIG. 5. An anode, formed by co-extrusion, is of sufficient thickness to support the fuel cell, and contains two concentric layers: inner layer 661 contains a higher volume percentage of an electrochemically active substance, and outer layer 662 contains a higher volume percentage of an electrolyte substance. Electrolyte layer 640 is able to be thinner than it would be if it had to support the fuel cell, and is thus of lower resistance than conventional electrolyte layers. Cathode layer 620 surrounds the electrolyte layer 640, and oxidizing gas 625 and fuel gas 665 flow on opposing sides of the tube. Since the anode layer (661 and 662) supports the cell, its thickness T3 may represent 50% or more of the total thickness of the cell (T1 plus T2 plus T3), and electrolyte layer 640 may be correspondingly thinner than in a conventional cell.

While the above description has described processes in which a cell-supporting anode is formed as the innermost layer of a tubular fuel cell, it is equally possible to produce a cell-supporting anode as the outermost layer of a tubular fuel cell, in accordance with an embodiment of the invention. In such a case, the process for manufacturing the anode is similar to that described above, except that an electrolyte layer and a cathode layer are coated on the inside of the anode layer after it has been extruded and sintered. Also, to manufacture such a cell by a co-extrusion process, a higher ratio of electrochemically active substance to electrolyte substance would be present at larger diameters of the anode (rather than smaller). In operation, a fuel gas (containing hydrogen) would be made to flow on the outside of the tubular fuel cell, while an oxidizing gas (containing oxygen) would be made to flow on the inside of the tubular fuel cell.

Further embodiments of the invention include electrode-supported oxygen pumps and oxygen sensors. Along with solid oxide fuel cells, solid state oxygen pumps and oxygen sensors are both examples of solid state electrochemical cells.

Solid state oxygen pumps are typically used to remove the oxygen gas component from a mixture of gases. For example, they enable oxygen gas to be removed from an $N_2/O_2$ mix, or from an Argon/$O_2$ mix.

Solid state oxygen sensors generate a voltage that depends on the partial pressure of oxygen in a gas with which they are in contact, and are commonly used to sense whether a car engine is running "fuel rich" or "fuel lean" by sensing oxygen levels in the car's exhaust.

Figure 7A:
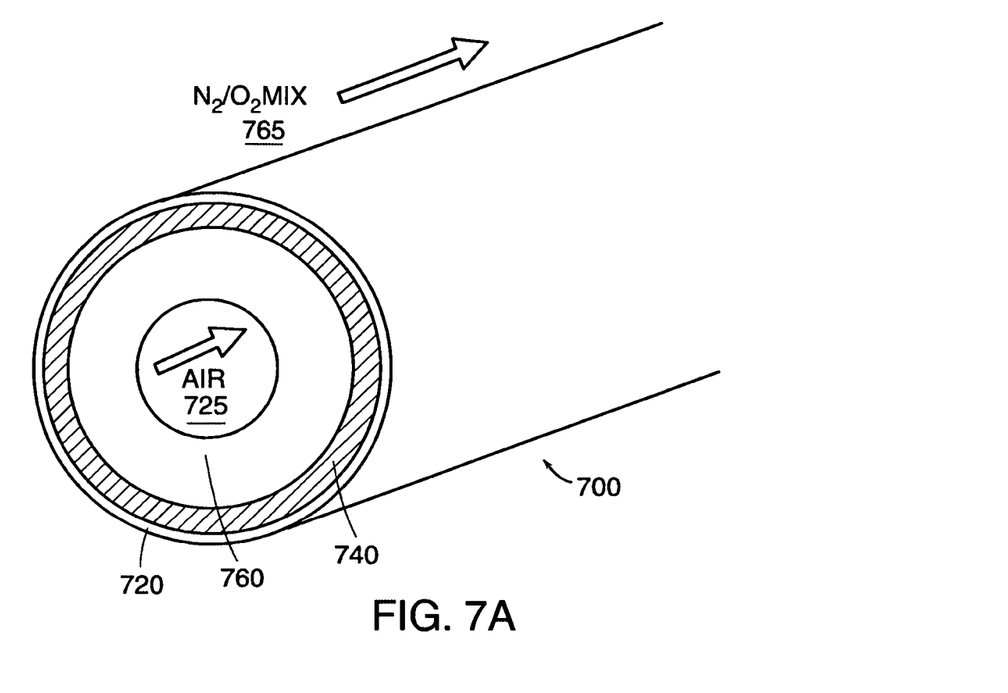
FIGS. 7A and 7B show an electrode-supported oxygen pump or oxygen sensor according to an embodiment of the invention.
Figure 7B:
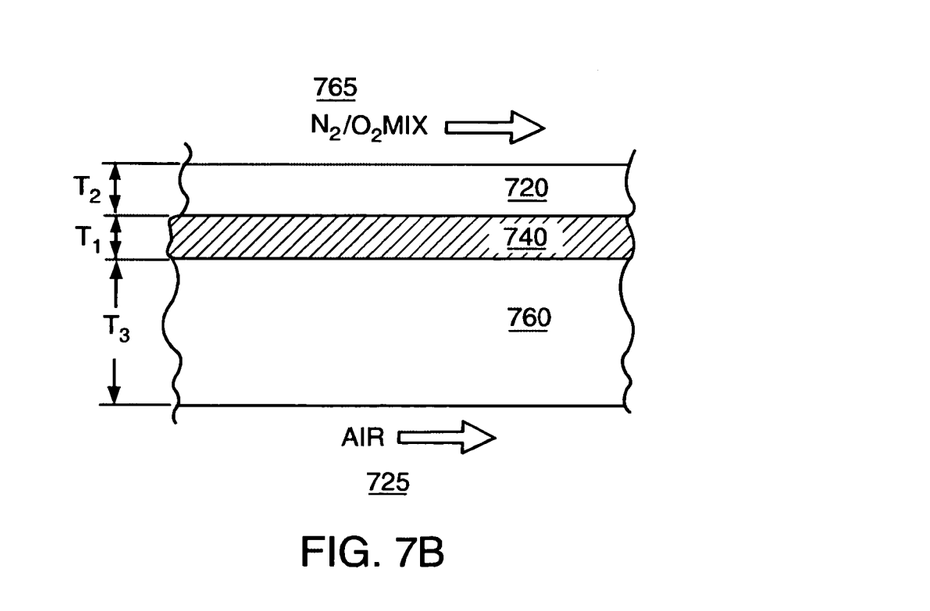

Oxygen pumps and oxygen sensors, which may be made in accordance with the embodiment of FIGS. 7A and 7B, both operate in accordance with the Nernst equation:

$$\varepsilon = \frac{RT}{n\mathcal{F}} \int_{PO_2'}^{PO_2''} t_i \, d\ln(PO_2) \quad \{\text{Equation 4}\}$$

for electromotive force $\varepsilon$, gas constant R, temperature T, n electrons transferred (e.g. 4 for $O_2$), Faraday's constant $\mathcal{F}$, transport number $t_i$, and oxygen partial pressures $PO_2'$ and $PO_2''$ on opposite sides of the cell layers. The transport number $t_i$ is given by $$t_i = \frac{\sigma_i}{\sigma_i + \sigma_e + \sigma_h} \quad \{\text{Equation 5}\}$$

for an electrolyte having ionic conductivity $\sigma_i$, electron conductivity $\sigma_e$, and hole conductivity $\sigma_h$. For an electrolyte that is a poor electronic conductor, but a good ionic conductor (i.e. when $\sigma_e$ and $\sigma_h$ are small compared with $\sigma_i$), the transport number is approximately 1 (as follows from Equation 5). This is the case, for example, when zirconia (a common electrolyte) is used as the electrolyte layer. For such a case, Equation 4 can be approximated as $$\varepsilon = \left(\frac{RT}{n\mathcal{F}}\right)\ln\left(\frac{PO_2'}{PO_2''}\right) \quad \{\text{Equation 6}\}$$

In an oxygen pump, an electromotive force $\varepsilon$ is applied across the terminals of the pump, thereby causing oxygen partial pressures $PO_2'$ and $PO_2''$ to adjust to the levels specified by the Nernst equation. Thus oxygen ions are pumped through the electrolyte layer; one oxygen partial pressure (for example that of the $N_2/O_2$ mix 765 in FIGS. 7A and 7B) is reduced, and another oxygen partial pressure (for example that of air 725 in FIGS. 7A and 7B) is increased.

Conversely, in an oxygen sensor, a gas containing a known partial pressure of oxygen, $PO_2'$, (for example air 725 in FIGS. 7A and 7B) is placed on one side of the sensor, and a gas containing an unknown partial pressure, $PO_2''$ (for example $N_2/O_2$ mix 765 of FIGS. 7A and 7B) is placed on the other side. The resulting electromotive force $\varepsilon$ may be measured as a voltage across the electrodes of the sensor.

FIGS. 7A (cross-sectional isometric view) and 7B (cross-sectional view) show an electrode-supported oxygen pump or oxygen sensor according to an embodiment of the invention. In this embodiment, tubular oxygen pump or sensor 700 is mechanically supported by a thick anode layer 760, upon which thin electrolyte layer 740 and cathode layer 720 are formed. As shown in FIG. 7B, anode layer 760 has a greater thickness $T_3$ than the thicknesses $T_1$ and $T_2$ of the electrolyte layer 740 and the cathode layer 720. Since the anode layer 760 supports the cell, its thickness T3 may represent 50% or more of the total thickness of the cell (T1 plus T2 plus T3), and electrolyte layer 740 may be correspondingly thinner. In alternative embodiments, pump or sensor 700 is mechanically supported by a thick cathode layer, upon which a thin electrolyte layer and anode layer are formed; or by both an anode and a cathode, of similar or equal thickness, with a thin electrolyte between. In any of these cases, since pump or sensor 700 is mechanically supported by an electrode (either anode 760, cathode 720, or both), there is no need for a thickened electrolyte layer to support the cell. Thus the thickness (1) of the electrolyte layer 740 may be less than it would be in an electrolyte-supported cell. As follows from Equation 1, a lower thickness (1) means that cell 700 has a lower resistance. Oxygen pumps and sensors according to this embodiment thus have a lower resistance than electrolyte-supported systems would have. A thinner electrolyte also allows low temperature use, and permits maximum flow of oxygen.

Alternative embodiments of oxygen sensors according to the invention may be configured to have the gas with an unknown partial pressure of oxygen flow through the center of the tube, while the gas with a known partial pressure of oxygen flows on the outside of the tube; or may be reversed, with the unknown gas flowing on the outside of the tube, and the known gas flowing through its center. Similarly, alternative embodiments of oxygen pumps may have the mixed gas flow through the center of the tube, with oxygen pumped outwards; or may have the mixed gas flow on the outside of the tube, with oxygen being pumped inwards. For both oxygen sensors and oxygen pumps, the two alternative configurations differ from each other by the relative placement of the anode and cathode (i.e. by whether the cathode is the innermost layer and the anode outermost, or vice versa).

In one embodiment according to the invention, an electrode-supported oxygen pump or oxygen sensor is manufactured by an analogous technique to that of the embodiment of FIG. 3 and of the manufacturing process "Example." However, instead of extruding a cell-supporting anode made of, for example, a mixture of nickel and YSZ, there is extruded a precious metal mixed with an electrolyte substance, to form an electrode capable of supporting the sensor or pump. The precious metal may include, for example, platinum, palladium, silver, rhodium, or rhenium; while the electrolyte substance may include, for example, YSZ. The precious metal need not be mixed with an electrolyte substance, but may alternatively be pure. To complete the manufacture of the pump or sensor, a YSZ electrolyte is layered onto the anode, in a similar fashion to that described for the embodiment of FIG. 3 and the manufacturing process "Example"; and then a layer of platinum is sprayed onto the electrolyte layer, to form the cathode.

In another embodiment, an electrode capable of supporting an oxygen pump or oxygen sensor is manufactured by extruding a porous perovskite, such as doped $LaCoO_3$ or doped $La[CoFe]O_3$.

In both the precious metal and perovskite embodiments, an electrolyte layer is layered around the first electrode, and a second electrode is layered around the electrolyte layer. The second electrode is preferably formed of the same material as the first electrode.

In one embodiment of an oxygen sensor or pump according to the invention, the electrolyte layer is made of YSZ, in a similar fashion to that described for the embodiment of FIG. 3 and the manufacturing process "Example."

In another embodiment, the electrolyte layer is made of a thin layer of YSZ (or other electrolyte substance) along with a porous support layer, such as an alumina layer.

In another embodiment, the electrolyte layer is made of doped cerium oxide ($CeO_2$), which may be doped with calcia or yttria. In this case, the surface of the electrolyte layer may be reduced (for example by passing a reducing gas over its surface) to form $CeO_{2-x}$, which is an N-type electronic conductor. The reduced layers on the electrolyte may thus play the role of electrodes, and there is no need for further separately layered electrodes to be applied. Alternatively, separate electrode layers may be applied, without reducing the surface of the electrolyte. Instead of $CeO_2$, doped $Ln_2O_3$, or other lanthanum oxides, may be used; or doped bismuth oxide ($Bi_2O_3$); yttrium oxide ($Y_2O_3$); or lead oxides (PbO).

In another embodiment, the electrolyte layer may be made of a porous perovskite, such as doped $LaCoO_3$ or doped $La[CoFe]O_3$.

It it to be understood that analogous features of oxygen pumps and oxygen sensors according to an embodiment of the invention are manufactured in an analogous fashion to that described for the fuel cell embodiments above. Layers may be applied by extrusion, co-extrusion, spraying, dipping, coating, or other methods as appropriate to the materials used.

It should also be noted that, for fuel cell, oxygen pump, and oxygen sensor embodiments, tubes may alternatively be manufactured in open- or closed-ended versions (with closed ends being formed, for example, by pinching an open end of an extruded tube).

In further embodiments of fuel cells, oxygen pumps, and oxygen sensors according to the invention, hollow tubes may be manufactured (for example, by extrusion) that have a non-circular cross-section. In one embodiment, the tube has a star-shaped cross-section, instead of a circular cross-section, but other cross-sections are possible. The cross-section used may be adjusted depending upon desired fuel cell packing density and thermal characteristics. Thus, it should be understood that where, above, reference is made to an inner diameter of a tube, similar considerations apply to an inner surface of a tube (for example where the tube's cross-section is non-circular).

Although this description has set forth the invention with reference to several preferred embodiments, one of ordinary skill in the art will understand that one may make various modifications without departing from the spirit and the scope of the invention, as set forth in the claims.

We claim:

1. A tubular solid oxide fuel cell comprising:
   a sintered tubular anode comprising an electrochemically active metallic substance and an electrolyte substance without a distinct pore forming substance, the electrochemically active metallic substance consisting essentially of reduced metal oxide;
   an electrolyte disposed on a surface of the tubular anode; and
   a cathode disposed on the electrolyte, wherein a thickness of the anode comprises over 50% of a total thickness of the anode, the electrolyte, and the cathode.

2. A fuel cell according to claim 1, wherein the anode is formed from a mixture of stabilized zirconia and nickel oxide.

3. A fuel cell according to claim 2, wherein the electrolyte comprises stabilized zirconia.

4. A fuel cell according to claim 1, wherein the anode comprises more than one anode layer, each layer having a different composition.

5. A fuel cell according to claim 4, wherein each of the anode layers comprises a ratio of electrochemically active substance to electrolyte substance, and wherein such ratios are higher for layers that are layered further from a surface of the anode that contacts a fuel gas than for layers that are layered closer to the fuel gas.

6. A fuel cell according to claim 5, wherein the electrochemically active substance is nickel and the electrolyte substance is stabilized zirconia.

7. A fuel cell according to claim 5, wherein there are two anode layers.

8. A fuel cell according to claim 4, wherein the more than one anode layers comprise a thicker support layer and a thinner active layer, the support layer being in contact with a fuel gas.

9. A fuel cell according to claim 8, wherein the support layer comprises a higher ratio of stabilized zirconia to nickel, and wherein the active layer comprises a lower such ratio.

10. A fuel cell according to claim 8, wherein the support layer comprises from 0% to 50% nickel by volume.

11. A fuel cell according to claim 8, wherein the active layer comprises from 40% to 45% nickel by volume.

12. A fuel cell according to claim 8, wherein the active layer comprises an embedded current-collecting wire.

13. A fuel cell according to claim 8, wherein the support layer comprises aluminum oxide.

14. A fuel cell according to claim 4, wherein the anode is formed by co-extruding more than one anode layer to form the tubular anode.

* * * * *